United States Patent [19]

Gerson et al.

[11] Patent Number: 4,694,022

[45] Date of Patent: Sep. 15, 1987

[54] FATTY ACID SALTS OF BETAXOLOL USEFUL IN THE TREATMENT OF GLAUCOMA

[75] Inventors: Steven H. Gerson; Wesley W. Han, both of Fort Worth, Tex.

[73] Assignee: Alcon Laboratories, Inc., Forth Worth, Tex.

[21] Appl. No.: 946,345

[22] Filed: Dec. 24, 1986

[51] Int. Cl.$^4$ .................. C11C 3/00; A61K 31/045; A61K 31/085
[52] U.S. Cl. .................................. 514/554; 260/413; 514/913
[58] Field of Search .................. 260/413 R; 514/554, 514/913

[56] References Cited

U.S. PATENT DOCUMENTS

| | | | |
|---|---|---|---|
| 4,136,178 | 1/1979 | Lin et al. | 514/913 |
| 4,252,984 | 2/1981 | Manoury et al. | 260/501.17 |
| 4,342,783 | 8/1982 | Morselli et al. | 514/913 |
| 4,522,829 | 6/1985 | Harting et al. | 514/913 |

*Primary Examiner*—J. E. Evans
*Attorney, Agent, or Firm*—James A. Arno; Gregg C. Brown

[57] ABSTRACT

Fatty acid salts of betaxolol, a cardioselective beta-blocker, and ophthalmic compositions containing these salts are described. These new salts have an aqueous solubility significantly less than that of betaxolol hydrochloride. This relatively poor aqueous solubility enables the salts to be slowly released from a suitable ophthalmic vehicle when placed in the aqueous environment of the eye. The salts also exhibit a significantly lower incidence of ocular irritation, as compared to ophthalmic solutions containing betaxolol hydrochloride.

6 Claims, No Drawings

FATTY ACID SALTS OF BETAXOLOL USEFUL IN THE TREATMENT OF GLAUCOMA

BACKGROUND OF THE INVENTION

1. Field of the Invention

The present invention relates to the field of topical glaucoma therapy. More particularly, this invention relates to certain fatty acid salts of 1-{4-[2-(cyclopropyl-methoxy)-ethyl]-phenoxy}-3-isopropylamino-propan-2-ol, which is also known as betaxolol. This compound is a known antiglaucoma agent. The use of this compound to treat glaucoma is described in U.S. Pat. No. 4,342,783; the entire contents of this patent are hereby incorporated in the present specification by reference. The structural formula of this compound and its method of preparation are described in U.S. Pat. No. 4,252,984, the entire contents of which are incorporated herein by reference. The hydrochloride salt of this compound is the active ingredient in BETOPTIC®, a topical ophthalmic preparation currently used in the treatment of glaucoma.

Betaxolol is a cardioselective, beta-adrenergic blocking agent. The cardioselectivity of this compound is a significant advantage in the treatment of glaucoma, because the incidence of pulmonary side effects with this compound is significantly less than with other known beta-blockers used in the topical treatment of glaucoma.

The present invention is directed toward improving two aspects of the topical ophthalmic use of betaxolol. First, the duration of action of the hydrochloride salt of betaxolol is approximately 12 hours, which means that a glaucoma patient must administer drops of an ophthalmic solution containing this form of betaxolol two or more times per day to the affected eye(s). The duration of action of betaxolol hydrochloride is believed to be directly related to the high aqueous solubility of this compound, which results in relatively rapid removal of the compound from the eye via the normal bathing of the eye by tears. It is therefore desired to provide a different form (i.e., salt) of betaxolol which is not as prone to this "wash out" effect, and as a result has a longer duration of action than betaxolol hydrochloride.

A second aspect of the current glaucoma therapy with betaxolol hydrochloride which the present invention is directed toward improving is the elimination of a stinging sensation experienced by some patients upon topical application of this form of betaxolol to the eye. This stinging sensation, although experienced in a minority of the patients treated, may interfere with a patient's compliance with prescribed therapy. The provision of a different form of betaxolol which has a therapeutic effect substantially equivalent to or better than that of betaxolol hydrochloride, but which does not cause a stinging sensation upon topical application to the eye, is therefore desired.

SUMMARY OF THE INVENTION

A principal objective of the present invention is the provision of a form of betaxolol which has a longer duration of action than betaxolol hydrochloride upon topical application to the eye.

Another objective of the present invention is the provision of a form of betaxolol which does not cause a stinging sensation when applied topically to the eye or result in any other form of ocular discomfort.

The foregoing objectives and other general objectives of the present invention are achieved by the provision of fatty acid salts of betaxolol. The aqueous solubility of these salts is significantly less than that of betaxolol hydrochloride. This relatively poor aqueous solubility enables these salts to be slowly released from a suitable vehicle when applied topically to the eye. The net effect of this reduced aqueous solubility is a significantly longer duration of action than betaxolol hydrochloride. The present salts of betaxolol are also much less likely to cause ocular discomfort when applied topically to the eye than betaxolol hydrochloride. The present salts of betaxolol and ophtalmic pharmaceutical compositions containing these salts are therefore believed to provide significant improvements in topical, ophthalmic betaxolol therapy.

DESCRIPTION OF PREFERRED EMBODIMENTS

The compounds of the present invention are represented by the formula:

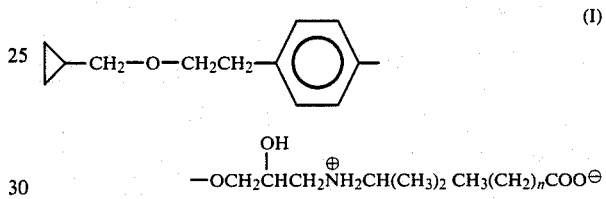

wherein n is a whole number of 10 or greater. These compounds may be described as being fatty acid salts of betaxolol. Compounds wherein n is 10, 14, 16, or 18 are particularly preferred. It has been found that n must be 12 or greater in order to reduce the aqueous solubility of betaxolol significantly.

The compounds of formula (I) may be prepared by reacting betaxolol base with a fatty acid of formula:

wherein n is a whole number of 10 or greater; the preparation of betaxolol base is described in U.S. Pat. No. 4,252,984, the contents of which have been incorporated herein by reference. This reaction may be performed by separately dissolving equimolar amounts of betaxolol base and a fatty acid of formula (II) in ether. The ethereal solutions formed by this initial step are then combined to form a single solution, and this solution is placed in a freezer at a temperature of −10° C. for 16 hours. A suspension of betaxolol fatty acid salt in ether is formed as the result of this step. This salt suspension is next removed from the freezer and allowed to warm to room temperature. The salt is then recovered by means of filtration, washed with ether and dried in vacuuo at 40° C.

The compounds of formula (I) may also be prepared by refluxing a solution containing a fatty acid of formula (II) with an equimolar amount of sodium hydroxide. The resulting solution is then cooled to room temperature and the sodium salt of the fatty acid is collected by filtration and dried at 50° C. Equimolar amounts of the fatty acid sodium salt and betaxolol hydrochloride, which is also drscribed in U.S. Pat. No. 4,252,984, are then dissolved in water and heated to 100° C. The salt which precipitates upon cooling to 0° C. is collected by filtration and dried in vacuuo at 50° C.

The above-described fatty acid salts of betaxolol are contained in the topical, ophthalmic compositions of the present invention in an amount of from about 0.25% to about 10% by weight. The concentrations utilized in these compositions will generally be higher than the concentrations of betaxolol hydrochloride or betaxolol base in analogous compositions because of the relatively poor aqueous solubility of the present compounds. As explained above, this limited solubility provides these compounds with an extended duration of action due to their delayed release from a suitable, pharmaceutically acceptable ophthalmic vehicle when placed in the aqueous environment of the human eye. The duration of action will vary depending on the particular salt employed and the type of ophthalmic vehicle utilized. A duration of action of 24 hours or more is preferred. Accordingly, a typical dosage regimen with the compositions of the present invention will comprise administering a therapeutically effective amount of an ophthalmic composition containing a compound of formula (I) topically to the affected eye once daily (i.e., once per 24 hours).

Because of the low aqueous solubility of the compounds of formula (I), the initial concentration of drug in the precorneal region of the eye will be very low compared to the initial concentration seen when a solution containing an equivalent amount of drug is placed in the eye. In order for a therapeutically useful amount of drug to be present in the precorneal region and ultimately in the aqueous humor, it is necessary that the compounds of formula (I) be delivered to the eye in an ophthalmic vehicle which is retained in the eye for a prolonged period. This retention may be achieved by utilizing a formulation which is retained in the eye either as the result of physical resistance to expulsion by tears, blinking or other natural actions of the eye, or as the result of an affinity of the formulation for ocular tissue. In addition to this retention requirement, the formulation must be aqueous or at least include a continuous aqueous phase in order to facilitate diffusion of dissolved drug and dissolution of undissolved drug.

With the foregoing requirements in mind, a number of suitable types of formulations will be apparent to those skilled in the art of ophthalmic drug delivery. Ophthalmic gels represent a preferred type of formulation, with polymeric gels being partucularly preferred. The polymers which may be utilized to form such gels include all polymers which: (1) are capable of demonstrating batch to batch uniformity; (2) do not demonstrate immunogenicity or other forms of toxicity; (3) are easily sterilized; and (4) are capable of producing a gel having adequate viscosity to facilitate retention of the gel in the eye. Carboxyvinyl polymers represent one example of polymers which are suitable for use in forming ophthalmic gels. Such gels are described In U.S. Pat. No. 4,271,143, the entire contents of which are hereby incorporated by reference in the present specification. Reference is made to this patent for further teaching regarding the use of polymers to form ophthalmic gels.

In addition to the above-described gel formulations, the compounds of formula (I) may also be delivered to the eye by means of oil in water emulsions or microemulsions, liposomes, lipopolysacchasomes, viscous suspensions, polysaccharides, bioretentive beads or bioadhesive polymers.

The compositions of the present invention may optionally comprise one or more ancillary ingredients, such as preservatives (e.g., benzalkonium chloride and thimerosal), surfactants (e.e., polyoxyethylene/polyoxypropylene copolymers and Tyloxapol), tonicity agents (e.g., sodium chloride, potassium chloride, and mannitol) and buffers (e.g., HCl and/or NaOH).

EXAMPLE 1

The following formulation is illustrative of the ophthalmic compositions of the present invention.

| Ingredient | Amount (Wt. %) |
|---|---|
| Locust Bean Gum | 1.25 |
| Xanthan Gum | 1.0 |
| Betaxolol Eicosanate | 1.0 |
| Thimerosal | 0.01 |

This composition may be prepared by combining all of the ingredients in powder form and then adding purified water or 0.9% sodium chloride solution to form a gel. The combined materials are heated at 75° C. for 30 minutes and then allowed to cool at room temperature.

What is claimed is:

1. A compound of formula:

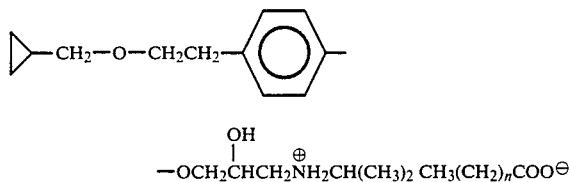

herein n is a whole number of 10 or greater.

2. A compound according to claim 1, wherein n is 10.
3. A compound according to claim 1, wherein n is 14.
4. A compound according to claim 1, wherein n is 16.
5. A compound according to claim 1, wherein n is 18.
6. A topical, ophthalmic composition comprising a compound of formula:

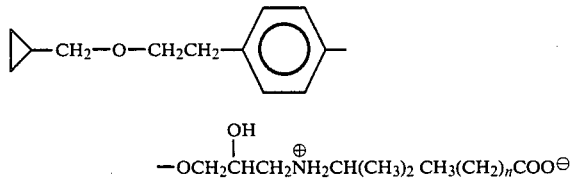

wherein n is a whole number of 10 or greater, in an amount effective to treat glaucoma by reducing intraocular pressure; and an aqueous, pharmaceutically acceptable, ophthalmic vehicle therefor.

* * * * *